United States Patent [19]

Marshall

[11] Patent Number: 5,510,267
[45] Date of Patent: Apr. 23, 1996

[54] FLOW CYTOMETRY LYTIC AGENT AND METHOD ENABLING 5-PART LEUKOCYTE DIFFERENTIAL COUNT

[75] Inventor: Paul N. Marshall, Santa Clara, Calif.

[73] Assignee: Abbott Laboratories, Abbott Park, Ill.

[21] Appl. No.: 934,282

[22] Filed: Aug. 24, 1992

Related U.S. Application Data

[62] Division of Ser. No. 352,106, May 15, 1989, abandoned.

[51] Int. Cl.$^6$ .................................................. G01N 33/48
[52] U.S. Cl. .............................. 436/63; 436/10; 356/39
[58] Field of Search .................................. 436/8, 519, 10, 436/17, 18, 63; 356/39; 435/2; 424/2, 3

[56] References Cited

U.S. PATENT DOCUMENTS

| | | |
|---|---|---|
| 3,874,852 | 4/1975 | Hamill . |
| 4,099,917 | 7/1978 | Kim .......................................... 436/10 |
| 4,102,810 | 7/1978 | Armstrong . |
| 4,185,964 | 1/1980 | Lancaster . |
| 4,284,412 | 8/1981 | Hansen et al. ............................ 436/519 |
| 4,286,963 | 9/1981 | Ledis et al. . |
| 4,465,774 | 8/1984 | Huang et al. .......................... 436/17 X |
| 4,485,175 | 11/1984 | Ledis et al. . |
| 4,577,964 | 3/1986 | Hansen, Jr. ................................. 356/39 |
| 4,617,275 | 10/1986 | Matsuda et al. . |
| 4,637,986 | 1/1987 | Brown et al. . |
| 4,654,312 | 3/1987 | Chang et al. .............................. 436/17 |
| 4,727,020 | 2/1988 | Recktenwald ............................ 436/519 |
| 4,743,678 | 5/1988 | Essex et al. ........................... 436/531 X |
| 4,745,071 | 5/1988 | Lapicola et al. . |
| 4,751,179 | 6/1988 | Ledis et al. ............................. 436/17 X |
| 4,902,613 | 2/1990 | Chang et al. .............................. 436/17 |
| 5,017,497 | 5/1991 | de Grooth et al. ........................ 436/63 |
| 5,039,613 | 8/1991 | Matsuda et al. ............................ 436/17 |

FOREIGN PATENT DOCUMENTS 0115077  8/1984  European Pat. Off. .

OTHER PUBLICATIONS

J. Neugebauer, "A Guide to the Properties and Uses of Detergents in Biology and Biochemistry," Calbiochem, LaJolla, 1987.
Ortho Marketing Publication on ELT–1500, 1985.
Ortho ELT–1500 Users Manual, 1985.
Technicon H * 1 Users Manual, 1986.

Primary Examiner—Robert J. Warden
Assistant Examiner—Hien Tran
Attorney, Agent, or Firm—Richard D. Schmidt

[57] ABSTRACT

A lytic agent is described which when mixed with whole blood, lyses the red cells instantly, but does not affect the optical, light scattering properties of the white blood cells for at least 30 seconds. This lytic agent enables the performance of a five part leukocyte differential by flow cytometry and light scattering. In its preferred embodiment, the lytic agent incorporates 2-phenoxyethanol which combines the functions of leukoprotective and antimicrobial, TRITON X-100 (octylphenoxypolyethoxyethanol) a lytic and wetting agent and TRIS/HCl to provide pH buffering and to increase the solution's conductivity.

6 Claims, 5 Drawing Sheets

FLOW CYTOMETRY LYTIC AGENT AND METHOD ENABLING 5-PART LEUKOCYTE DIFFERENTIAL COUNT

This application is a division of application Ser. No. 07/352,106, filed May 15, 1989, now abandoned.

TECHNICAL FIELD

This invention relates generally to reagents and methods useful in flow cytometry measurement of red and white blood cell populations, and more specifically, to the use of a lytic agent containing an aromatic oxyethanol acting as a red blood cell lyse and white blood cell sheath and simultaneously as an antibacteriostat, enabling a five subpopulation differentiation of leukocytes in an automated instrument.

BACKGROUND OF THE INVENTION

The examination of the peripheral blood is an important aspect in evaluating the health of the individual. An important parameter within this examination is the differential white cell (or leukocyte) count. This test is presently performed in one of three ways. The most traditional method involves the preparation of a blood smear which is then stained via the Romanowsky method. This stain differentially colors the different constituents of whole blood. A technologist can enumerate the various leukocyte classes, typically neutrophils, lymphocytes, monocytes, eosinophils, and basophils by microscopic examination of the stained blood smear. As this manual differentiation is very labor intensive, substantial research and development effort has been expended to obtain an automated procedure for the examination of blood samples.

Recently multi-subpopulation leukocyte differential analysis has been routinely obtained with automated microscopes. These automated microscopes include the Hematrak series of products manufactured by Geometric Data (Wayne, Pa.) and the Diff 350 and 400 produced by Coulter Biomedical (Concord, Mass.). When these instruments are presented with a Romanowsky stained blood smear, using an image analyzing computer, these instruments can locate and classify white blood cells using visual classification criteria similar to those used by the human technician. These criteria typically include nuclear and cytoplasmic optical density, color, shape, and texture.

Another approach to automation of leukocyte differential involves the use of flow cytometry. In this procedure, blood cells in suspension are passed through a transducer and the cells are classified on the basis of some measurable parameter such as light absorption, light scatter or electrical impedance. The advantages of these flow cytometry systems compared to microscope-based systems include relatively high sample throughput and the ability to count larger number of cells per sample thereby reducing sampling noise. Commercial clinical flow cytometers have been limited, thus far, to three leukocyte subpopulation differential. Leukocytes are classified in subpopulations called granulocytes, monocytes and lymphocytes. The current three part differential instruments are based on either measurement of light scatter or electrical impedance. Light scatter instruments such as ELT 1500 of Ortho Instruments (Westwood, Mass.) classify white blood cell subpopulations on the basis of their light scattering characteristics measured at two different angles, typically termed "low" and "orthogonal." Electrical impedance instruments such as the S+ series of Coulter Electronics (Hialeah, Fla.) and Cell Dyn 2000 of Sequoia-Turner Corporation, (Mountain View, Calif.), classify leukocytes based on their volume following exposure to a volume modifying reagent.

Until recently, the only commercial clinical flow cytometry instruments capable of obtaining a five-subpopulation leukocyte differential were the H-6000 and H*1 of Technicon Instruments (Tarrytown, N.Y.) These instruments classify leukocytes by measuring light scatter and absorption after elaborate cytochemical staining of the blood cells. Since this staining process is relatively slow, the throughput of these instruments is compromised.

Cell-Dyn 3000 of Sequoia-Turner Corp. (Mountain View, Calif.) performs a conventional five subpopulation differential based only upon light scattering characteristics of unstained leukocyte cells. Since inherently slow cytochemical staining is not used, the sample throughput of this instrument is kept extremely high. The advances made possible by Cell-Dyn 3000 are largely the result of the combination of two innovations, namely measurement of depolarized orthogonal light scatter and the lytic agent of the present invention, enabling better resolution of lymphocytes and monocytes to obtain a five-subpopulation leukocyte differential analysis.

In commercially available automated instruments using flow cytometry, the leukocyte classification and differentiation is obtained either by light scatter or by electrical impedance related to cell size. In either type of instrument, the red blood cells in the whole blood sample must be lysed to release the hemoglobin. In electrical impedance measurement-based systems, quaternary ammonium-salt-based lysing agents have been used. These electrical impedance systems have an adequate response time which substantially nullifies the lytic effect of the lysing agent on the leukocytes. In light scattering measurement-based systems, the adverse effect of the red blood cell lysing agent upon the light scattering characteristics of the white blood cells is more severe, and thus more demanding from a design perspective. Lytic agents (used herein interchangeably with "lysing agents") must rapidly lyse red blood cells while simultaneously providing a window in which white blood cell light scattering characteristics are essentially undisturbed.

These criteria are typically met using a lytic agent with an alkaline pH, since the range of lysis of both red blood cells and white blood cells increases with pH. The widely used ammonium chloride/potassium bicarbonate/diNaEDTA lysis solution has a pH of 7.2–7.4, but typically takes 5–10 minutes to completely lyse red blood cells. Lytic agents such as Ortho Instruments, "Lyse Right" have a pH of ~8.5 and require several seconds to effect complete lysis of red blood cells, but will adversely affect the light scattering characteristics of white blood cells within a period of a minute, or so. When the pH is raised much above this, or lowered below about 3, lytic agents are obtained that lyse both red blood cells and white blood cells almost instantaneously.

Therefore, it is an object of this invention to provide a lytic agent which adequately lyses red blood cells while preserving the light scattering characteristics of the white blood cells for the period of time adequate to obtain subpopulation differentiation.

It is a further object of this invention to provide a lytic agent which enables the enumeration of five leukocyte subpopulations, identified as neutrophils, lymphocytes, monocytes, eosinophils and basophils, in a flow cytometry, light-scattering system.

It is another object of this invention to provide a lyric agent which has a commercially acceptable shelf life.

These and further objects of the present invention will become apparent to those of skill in the art with reference to the specification and figures.

SUMMARY OF THE INVENTION

The flow cytometry lytic agent of the present invention enables a five part differential enumeration of leukocytes into subpopulations identified as neutrophils, lymphocytes, monocytes, eosinophils and basophils. The lytic agent consists of an aqueous solution of an aromatic oxyethanol, an organic buffer, having pK at or near 8.5, which serves to provide pH buffering capacity and to increase electrical conductivity of the lytic agent, and a non-ionic detergent component. The aromatic oxyethanol is preferably 2-phenoxyethanol. The organic buffer is selected from the group consisting of TRIS/HCl buffer, boric acid, glycyl/glycine and BICENE buffer (N,N-bis(2-hydroxyethyl)glycine. The non-ionic detergent is selected from the group consisting of TRITON-X 100, TRITON X-114, polyoxyethylene or saccharide-derived detergents. The preferred lytic agent consists essentially of 2-phenoxyethanol at a concentration between 20 mM and 80 mM, TRIS/HCl buffer and TRITON X-100 (octylphenoxypolyethoxyethanol).

The method of the present invention provides the lytic agent as described above in combination with a diluted whole blood sample. After the addition of the lytic agent to the diluted whole blood sample, the red and white blood cells are intersected with a focussed laser beam. Four light scattering parameters are then measured at 0 degrees, 10 degrees, 90 degrees, and 90 degrees depolarized. These measured parameters are thereafter resolved to obtain a five part subpopulation differential enumerating the neutrophils, lymphocytes, monocytes, eosinophils, and basophils.

DETAILED DESCRIPTION OF THE INVENTION

In the preferred embodiment, the lytic agent comprises an aqueous solution of TRITON X-100 (octylphenoxypolyethoxyethanol), 2-phenoxyethanol, and TRIS/HCl buffer. Whole blood is mixed with an excess of this lytic reagent, typically a 50-fold excess. Lysis of the red blood cells occurs instantly due to the combination of osmotic shock, the action of the non-ionic detergent and pH of about 8.5. The 2-phenoxyethanol in the lytic agent serves two functions. Firstly, it functions as a leukoprotective reagent to retard lysis of lymphocytes, enabling detection of the subpopulations prior to substantial adverse effects on the white blood cells' optical properties caused by the lytic agent. Secondly, 2-phenoxyethanol functions in its more common role as an antimicrobial, allowing the reagent to remain free of microbial contamination for at least one year after preparation. The TRIS/HCl, a buffer commonly used in biochemical solutions, in addition to providing pH buffering capacity, serves to increase the conductivity of the solution so that its presence in the reagent reservoir of the instrument may be readily detected using a pair of electrodes. The TRITON X-100 (octylphenoxypolyethoxyethanol) serves as a wetting agent, reducing the hang up of air bubbles in the Cell-Dyn 3000 tubing and optical transducer.

The optimal formulation of the lytic agent is given below:
2-phenoxyethanol (a liquid at 25' C) . . . 750 mL TRIS/HCl buffer, pH 8.5 (500 mM TRIS buffer titrated to pH 8.5 with 1M HCl) . . . 1500 mL 0.5% (vol/vol) aqueous TRITON X-100 detergent (octylphenoxypolyethoxyethanol) . . . 100 mL Deionized water to . . . 100 L In the optimized formulation, 2-phenoxyethanol is present at a concentration of about 41 mM, although a useful range of concentrations exists between 20 and 80 mM. The pH of the TRIS buffer may be decreased to pH 8.1 without significant effects on its performance. If increased above pH 9.0, partial destruction of white blood cells can occur. The presence of trace amounts, up to about 5% (vol./vol.) of TRITON X-100 (octylphenoxypolyethoxyethanol), or a similar non-ionic detergent, prevents problems caused by inadequate lysis in specimens typically regarded as difficult to lyse. These include whole blood samples from patients with hemoglobinopathies and from those with elevated red blood cell counts.

Other organic buffers can be substituted for TRIS/HCl buffer. Among those with pK at or near 8.5, boric acid, glycylglycine and BICINE (available through CalBiochem) can be used in the lytic agent of the present invention. With respect to the non-ionic detergent component of the lytic agent, Triton X-114 can be used. Other hydrophilic detergents can be selected from those having polyoxyethylene or saccharide head groups.

The optimized formulation enables a five-part leukocyte differential to be obtained, using the light scattering properties of these cells. The Cell-Dyn 3000 measure four light scattering parameters on each leukocyte as it intersects a focussed laser beam. These parameters are:

(1) "0 degree light scatter" which is actually light scattered at about 1–3 degrees with respect to the laser beam.

(2) "10 degree light scatter" which is actually light scattered at about 3–10 degrees with respect to the laser beam.

(3) "90 degree light scatter" which is light scattered orthogonally to the laser beam.

(4) "90 degree depolarized light scatter" which is light scattered orthogonally to the laser beam, which by interaction with white cells is no longer vertically polarized.

We found that 2-phenoxyethanol was an effective leukoprotective agent as well as its more common use as an antimicrobial. In addition, 2-phenoxyethanol produced much better resolution of lymphocytes and monocytes by flow cytometry light scattering methods. In fact, with 2-phenoxyethanol a four part differential, i.e. lymphocytes, basophils, monocytes, neutrophils+eosinophils, can be obtained simply on the basis of low angle and orthogonal light scatter. Prior to this, only a three part leukocyte differential had proved possible using these two parameters. This phenomenon may be observed in certain instruments, produced by Ortho Diagnostic Systems, Inc. such as the ELT 1500.

Although a simple aqueous solution of 2-phenoxyethanol in water is an effective lytic agent, the electrical conductivity of this reagent is too low if the presence of the lytic reagent in instrument reservoirs is to be detected electrically. We therefore incorporated a TRIS/HCl buffer into our lytic agent to raise the conductivity of the lytic reagent solution and to stabilize pH. To minimize the incidents of problems due to partial white blood cell lysis, we have also incorporated trace amounts of a non-ionic buffer, TRITON X-100 (octylphenoxypolyethoxyethanol) into our formulation. This chemical also increases the wetting properties of the lytic agent in the reagent lines.

Figure 1:
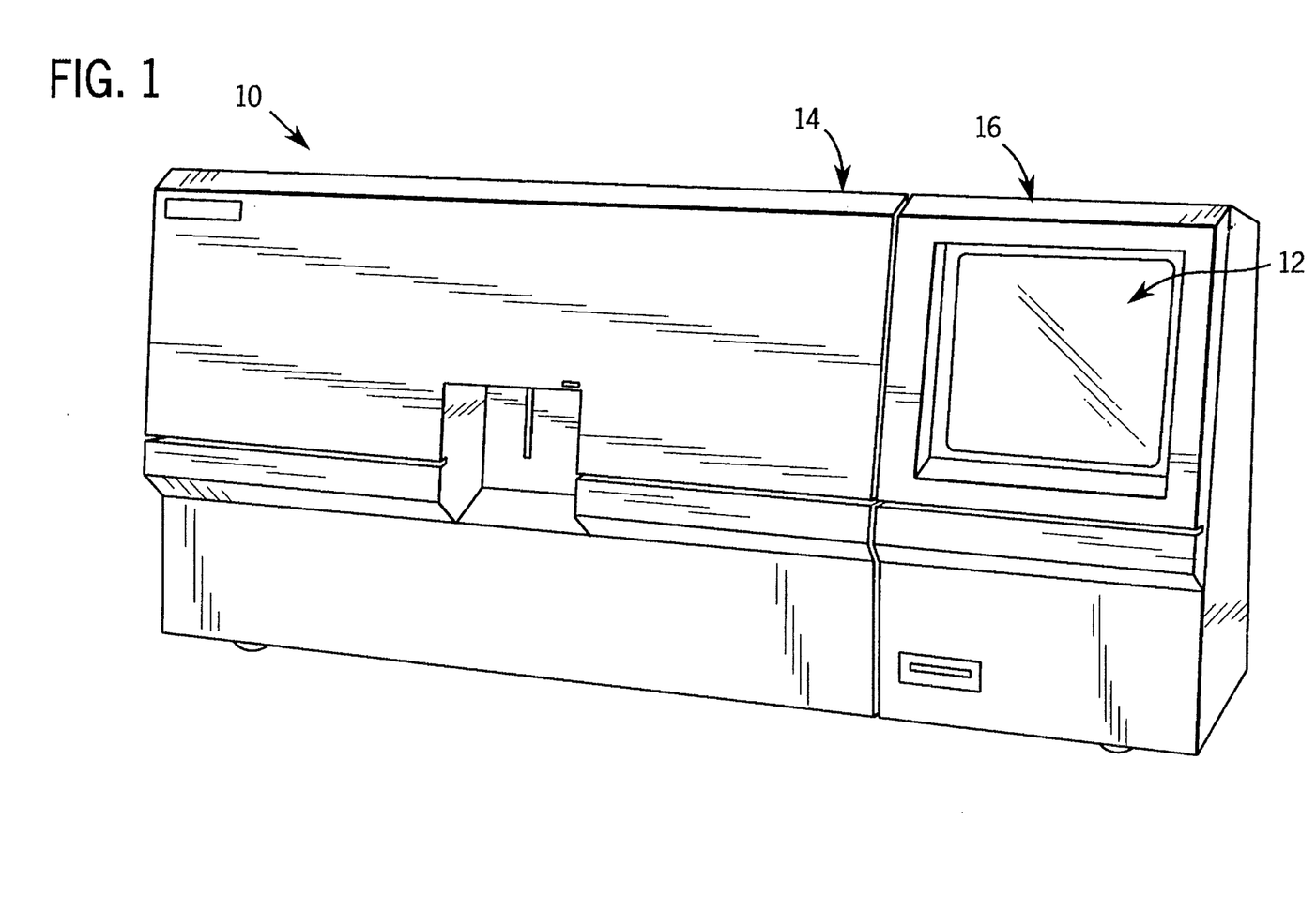
FIG. 1 is a perspective view of the Cell-Dyn 3000 automated hematology instrument which practices the present invention.

Turning now to the Cell-Dyn 3000 instrument 10 itself (see FIG. 1), a pair of transducers are used for cell measurement. White blood cells are measured by light scatter. In this channel, fluid metering is via syringe pump. Red blood cells and platelets are measured by their electronic impedance. In this channel a volumetric metering tube is used.

CELL-DYN 3000 operations are controlled by three microprocessors which monitor system status, store data, run QC programs, flag abnormal data and perform diagnostic checks.

The user can select any of eight modes using screen 12 labels. Any mode may be obtained using either the membrane keyboard, or full PC keyboard. The primary operating modes are as follows:

SETUP—to set up or revise system operation

RUN—to run specimens and controls

DATA LOG—to review or print stored data

QC—to review or print data in control or replicate files

CALIBRATION—to review or run user calibration

DIAGNOSTICS—to perform system checks for troubleshooting

HELP—to assist user in the operation of the instrument

SPECIAL PROTOCOLS—to run special procedures such as cleaning the sample valve or priming the sample lines For ease of transport, the CELL-DYN 3000 is divided into two modules. The main module 14 is constructed so that mixing chambers, valves, pumps, hemoglobin flow cell and the impedance transducer are all readily accessible at the front of the instrument 10. The back of the instrument contains two microprocessors. The upper compartment contains an optical bench on which are mounted lenses, laser, photodetectors and fused-silica flow cell. See FIG. 4. The second module 16 comprises the video monitor, PC and keyboard.

The CELL-DYN 3000 uses three transducers to collect data on blood cells and hemoglobin concentration. These are designated the impedance transducer, the optical transducer and the hemoglobin transducer.

Figure 2:
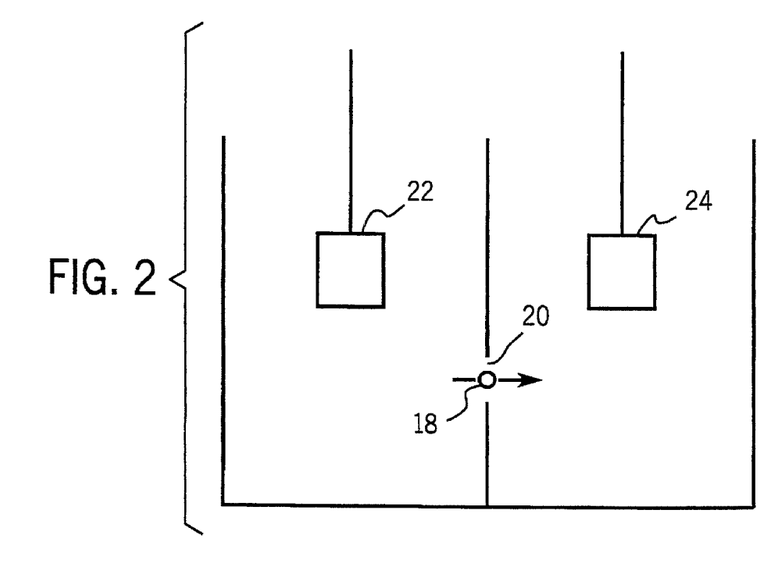
FIG. 2 Is a schematic representation of the principle of impedance cell counting and size.

The CELL-DYN 3000 uses an impedance transducer to count red blood cells and platelets. FIG. 2 illustrates the principle of impedance cell counting and sizing. The principle is based on the measurement of changes in electrical resistance produced by a particle 18 as it passes through a small aperture 20. As each cell traverses the aperture 20, the electrical resistance of the path between the submerged electrodes 22 and 24, which are located on either side of the aperture 20, increases. The number of pulses is indicative of cell count, the amplitude of the pulse is related to cell volume. Frequency distributions of pulse amplitude constitute volume histograms. These histograms are used to obtain red blood cell and platelet parameters such as MCV (mean cell volume) and RDW (red cell distribution width.)

In the CELL-DYN 3000 the impedance aperture 20 is 60 µm in diameter and 70 µm in length.

Figure 3:
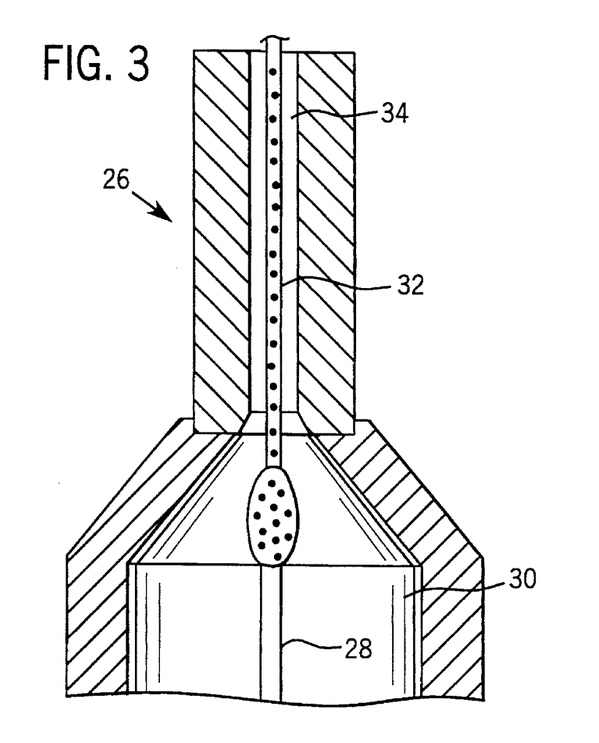
FIG. 3 is a cross sectional, schematic view of the optical transducer of the Cell-Dyn 3000 instrument.

The CELL-DYN 3000 uses an optical transducer to measure the light scattering characteristics of white blood cells. The transducer 26 is shown diagrammatically in FIG. 3. A suspension of blood in which the red blood cells have been lysed is propelled at low velocity from the sample nozzle 28 where it comes into contact with a fast moving, laminar flow, sheath stream 30. In a process known as hydrodynamic focussing, the sample stream is attenuated to a central core 32. In the fused silica flow cell this core is 25–30 µm in diameter. This arrangement ensures that usually only a single white blood cell is in the sensing region at any time and therefore coincidence problems are minimized. In addition, since the physical aperture is large (250 µm square) the flow cell 34 is unlikely to clog, yet it still gives the resolution of a much smaller transducer.

Figure 4:
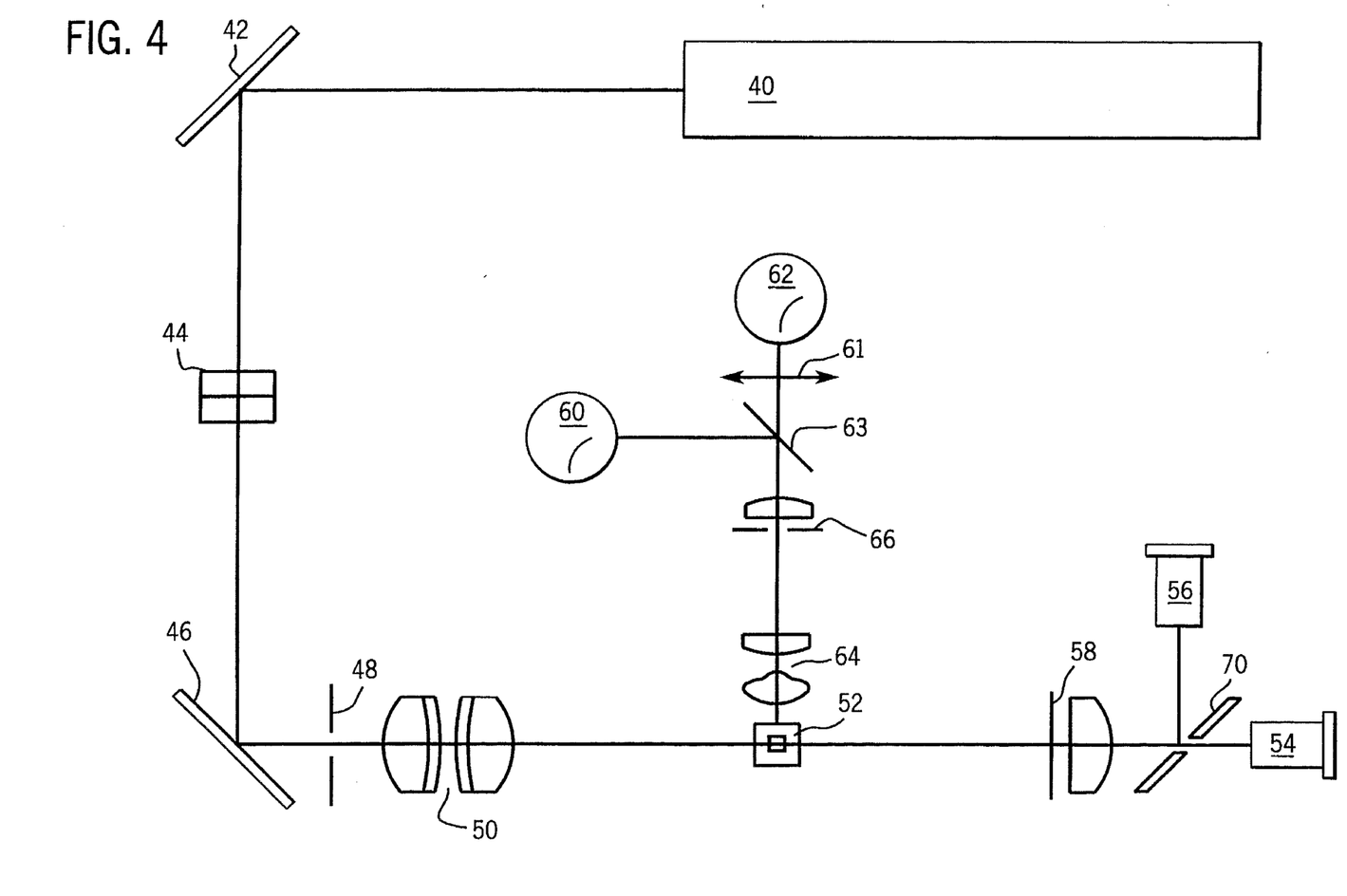
FIG. 4 is a schematic representation of the optical bench of the Cell-Dyn 3000 instrument.

A brief description of the CELL-DYN 3000 optical bench will be presented here to facilitate understanding the functioning of the white blood cell measurement process. A plan of the CELL-DYN 3000 optical bench is shown in FIG. 4. The specification of our co-pending, commonly assigned U.S. patent application Ser. No. 07/327,416, entitled PARTICLE DISCRIMINATOR AND METHOD, is herein incorporated by reference. The light source 40 is a polarized 5 mW helium-neon laser of wavelength 632.8 nm. The laser head is oriented so that the plane of polarization is vertical. The laser beam is shaped and focussed by front surface mirror 42, cylindrical lens 44, front surface mirror 46, vertical slit 48, and lens 50 so that in the region of the central core 52 of the sample stream the beam intensity profile in vertical plans is Gaussian with a ('one over e squared') diameter of about 70 um. In the horizontal plane the profile shows a 'top hat' appearance, with the flattened top being about 80 um. This arrangement insures that the instrument will continue to give reliable data even when the sample core wanders slightly from its normal position.

A white cell entering the focussed laser beam will scatter light in all directions. Since the wavelength of the light is small compared with the cell size, this scattering phenomenon is described by Mie theory. Only part of the scattered light is collected by four photodetectors. Two silicon photodiodes 54 and 56 measure light scattered at half angles of about 1–3 degrees and about 3–10 degrees with respect to the laser beam. These photodiodes 54 and 56 are termed the '0 degree' and '10 degree' detectors, respectively. Direct laser light is blocked with the obscuration bar 58. Light scatter at these low angles is some complex function of cell size. Light scattered at 90 degrees to the laser beam is also collected using two photomultipliers 60 and 62 (PMTs). PMTs, not photodiodes, are used in the 90 degree channel because relatively little light is scattered at high angles. One of the PMTs 62 has a horizontal polarizer 61 in front of it. Since this will prevent vertically polarized light from striking the photocathode, any light detected by the '90 degree' depolarized' PMT 62 is light that has been depolarized by its interaction with the white blood cell. The second photomultiplier 60 termed the '90 degree' PMT receives light reflected off a coverglass 63 angled at 45 degrees. The major proportion of this light is still vertically polarized.

An objective lens 64 and scatter stop 66 complete the orthogonal scatter channels. The low angle scatter channels also include a perforated mirror 70.

Data from the four photodetectors is used to construct a pair of scattergrams representative sample being shown in FIGS. 5 through 8. White blood cells can thus be separated into five subpopulations solely on the basis of light scatter.

For the red blood cell analysis, hemoglobin is converted to a heme-cyanide complex and measured by determination of absorbance at 550 nm in a ~1 cm pathlength flow cell.

In the Cell-DYN 3000, whole blood (120 µL, open tube; 250 µL closed tube) is aspirated via the specimen probe or cap piercer into a shear valve that isolates three precise aliquots. These aliquots are diluted with the appropriate diluent reagents and moved towards the transducers. At present, we use a diluent having the following composition in an aqueous solution: NaCl, 7.9 g/L, KCl, 0.4 g/L, $NaH_2PO_4$, 0.2 g/L, $Na_2HPO_4$, 1.9 g/L, $Na_2EDTA$, 0.3 g/L, NaF, 0.4 g/L, 2-phenoxyethanol 3 ml/L and water to make 1 liter. The diluent has pH 7.4±0.05, and an osmolality of 340±3 mohs. A 32 µL segment is sheared and diluted 250 times with the lytic agent of the present invention and transported to the optical transducer for determination of the white blood cell count and leukocyte differential. A 12 µL segment is sheared, diluted 250 times with hemoglobin reagent and transported to the hemoglobin transducer. The hemoglobin reagent is a mixture of a quaternary ammonium salt/KCN solution with the diluent noted above. In the best mode, the quaternary ammonium salt solution consists of tetradecyltrimethylammonium bromide 90 g/L and potassium cyanide 0.75 g/L, mixed into 1 liter of deionized water. Then, 1 liter of the quaternary ammonium salt solution is mixed with 11 liters of the diluent described above. Finally, TRITON X-114 is aded at a concentration of 0.25 mL/L. A 0.8 µL segment is diluted 12,500 times with red blood cell diluent and transported to the impedance transducer for measurement of red blood cells and platelets.

Each pulse resulting from a particle passing though the sensing zone is amplified and compared to internal reference voltages. In this way, white blood cells are discriminated from red blood cell stroma and platelets in the white blood cell channel. In a similar manner, red bloods cells and platelets are discriminated in the red blood cell/platelets channel.

To make absolute blood cell counts, the volume of diluted blood passing through the transducer during data acquisition must be known. For the red blood cell/platelet channel, this is achieved using a metering tube. During each count cycle, as cells are drawn through the impedance aperture, fluid is drawn through the metering tube. As the reagent meniscus passes an optical detector, the count cycle is started. The count cycle is stopped when the meniscus passes a second optical detector, after exactly 200 µL of diluted blood has passed through the transducer. The count time can be used to detect debris in the orifice, since such material will reduce the effective aperture and increase count time. This debris might adversely affect sizing data.

In the white blood cell channel, fluid metering is done using a syringe pump. Since the narrowest passageways in the white blood cell channel are relatively large (sample nozzle, ~160 µm diameter; fused silica flow cell, 250 µm square), debris accumulation is much less likely to occur.

It is possible that more than one cell particle may be present simultaneously in the sensing zone during counting. If ignored, this coincidence will artificially educe the cell count. Coincidence is directly related to the effective volume of the orifice and cell concentration and can therefore be corrected for mathematically. This is performed automatically for each white blood cell, red blood cell and platelet count.

CELL-DYN 3000 automatically displays all numeric and graphic data after each measurement cycle. Specimen measurements are performed by selecting the run mode. The specimen may be identified as any one of five types, namely: patient, low control, normal control, high control, replicate. Operator I.D., data, time, etc. may be entered via the keyboard. Displayed data may be printed on Z-fold paper (8.5"×11") via a graphics printer, a single report to the page. A multicopy ticket report can also be printed via an optional ticket printer.

Numeric data for the current 1,000 cycles is automatically stored on the PC hard disk. This data log may be reviewed or printed as required. Each data file includes a sequence number, specimen type, specimen I.D. # if used, numeric data for all selected parameters, date, time and operator I.D.

Using the setup mode, the user may set limits for any numeric data. Any data falling outside these limits are displayed in inverse on the video screen and are printed in bold type. When histogram data for platelets, or scattergram data for white blood cells do not meet certain criteria, each affected area is flagged with a region alert.

At the completion of each measurement cycle, the results are displayed on the monitor. Light scatter data from white blood cells are displayed as a pair of scattergrams. The absolute white blood cell count is displayed in units of thousands/µL of whole blood. The red blood cell data is displayed as a volume frequency distribution histogram with the abscissa calibrated in femtoliters. The absolute red blood cell count is displayed in units of millions/µL of whole blood. Platelet data is displayed as a volume frequency distribution histogram with the abscissa in femtoliters. The absolute platelet count is reported in units of thousands/µL of whole blood.

The CELL-DYN 3000 measures hemoglobin as a heme-cyanide complex. The hemoglobin reagent is an alkaline solution of a cationic detergent and potassium cyanide. The detergent lyses red blood cells causing hemoglobin release. At high pH, the hemoglobin releases heme chromophores which react with the cyanide present to form a stable complex. This is measured by its absorbance at 540 nm against a reagent blank. The hemoglobin result is reported in terms of its concentration in whole blood. The user may select any of the following units: g/dL, g/L. mmol/L.

CELL-DYN 3000 determines mean cell volume (MCV) from the red blood cell size distribution. The result is reported directly in femtoliters. The hematocrit (HCT) is calculated from the red cell count and MCV as follows:

$$HCT = (RBC\ count \times MCV)/10$$

The result is reported as percent packed red cells or as the proportion of packed red cells per unit volume of whole blood: L/L.

Red cell distribution width (RDW) is determined from the red cell volume distribution. It is simply the c.v. of the peak, expressed as percent [c.v.=(s.d./mean×100]. This parameter is an index of red cell heterogeneity. The RDW increases with the degree of anisocytosis seen on the blood smear. Diagnostically useful information may be obtained by reviewing both MCV and RDW.

The five-part white blood cell differential is determined solely on the basis of light scatter. Since no cytochemical staining is required, the CELL-DYN 3000 realizes an extremely high throughput (CBC/PLTs/WBC diff at a rate of 109/hour). The lytic agent of the present invention lyses red blood cells instantly, but does not affect the light scattering characteristics of white blood cells within the relevant measurement time. Data on the scatter characteristics of each white cell is obtained from four photodetectors. The '0 degree' detector collects light scattered at a half angels of about 1–3 degrees to the laser beam. The '10 degree' detector collects light scattered at a half angle of about 3–10 degrees. Scatter at low angles such as these is a function of cell volume. Scatter at high angles, such as perpendicular to the laser beam is function of the total amount structure in the cell: its 'structuredness.' All other things being equal, the high angle scatter of a cell will increase as, for example, the lobulation of the nucleus increases or as cytoplasmic granulation increases. The CELL-DYN 3000 uses two photomultiplier tubes to collect '90 degree' scatter and '90 degree depolarized' light scatter. In our application, at least, this depolarization signal results from multiscattering phenomena within the white blood cells. It is not an artifact of cross depolarization or autofluorescence.

Clinical usefulness of these new parameters—mean platelet volume [MPV], platelet distribution width [PDW] and plateletcrit [PCT] has not yet been established. Controversy exists regarding published findings. Currently in the U.S., FDA regulations prohibit the reporting of these parameters until clinical utility is established. Elsewhere, these results can be reported, as required. If MPV data is required, it is strongly recommended that specimens should be run at least one hour after collection, by which time the MPV will have stabilized. Generally, for about the first hour after collection into EDTA, MPV is increasing.

The CELL-DYN 3000 calculates MPV from the platelet histogram, to which a log-normal curve has been fitted. This parameter is reported directly in femtoliters. PCT is calculated from the platelet count and MPV as follows:

$$PCT=(PLT \times MPV)/10$$

The result is reported as percent or in mL/L. The PDW is the geometric s.d. of the platelet size distribution. It is derived from the platelet histogram data and reported as 10(g.s.d.).

These red cell indices are useful indications of red blood cell morphology and are useful in the classification of anemias. In addition, the index data for a particular specimen or collection of specimens, is very stable and should not change significantly over the long term, even though the values used to calculate each may have altered significantly. Because of this stability, the red blood cell indices may be used to quality control instrument performance. Bull's moving average QC program utilizes this principle.

Mean cell hemoglobin (MCH) and mean cell hemoglobin concentration (MCHC) whenever appropriate are parameters that are measured. The following equations apply:

$$MCH=(HGB/RBC\ count) \times 10$$

$$MCHC=(HGB/HCT) \times 10$$

MCH is reported in picograms or femtomoles. MCHC is reported as g/L, g/dL or mM/L.

EXAMPLE 1

Figure 5:
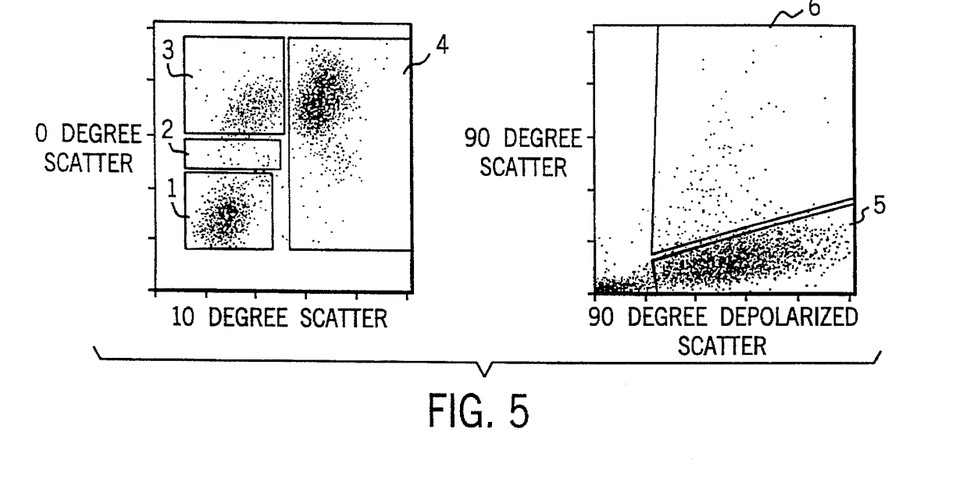
FIG. 5 is a white blood cell scattergram for the whole blood sample described in Example 1.

Referring to FIG. 5, scattergrams illustrating laser light scattering properties of whole blood from a normal donor after admixture with lytic agent described in this patent.
Scattergram on left
  Y axis: 0 degree scatter
  X axis: 10 degree scatter
Scattergram on right
  Y axis: 90 degree scatter
  X axis: 90 degree depolarized scatter
1=lymphocytes, 2=basophils, 3=monocytes, 4=neutrophils and eosinophils, 5=neutrophils, 6=eosinophils.

EXAMPLE 2

Figure 6:
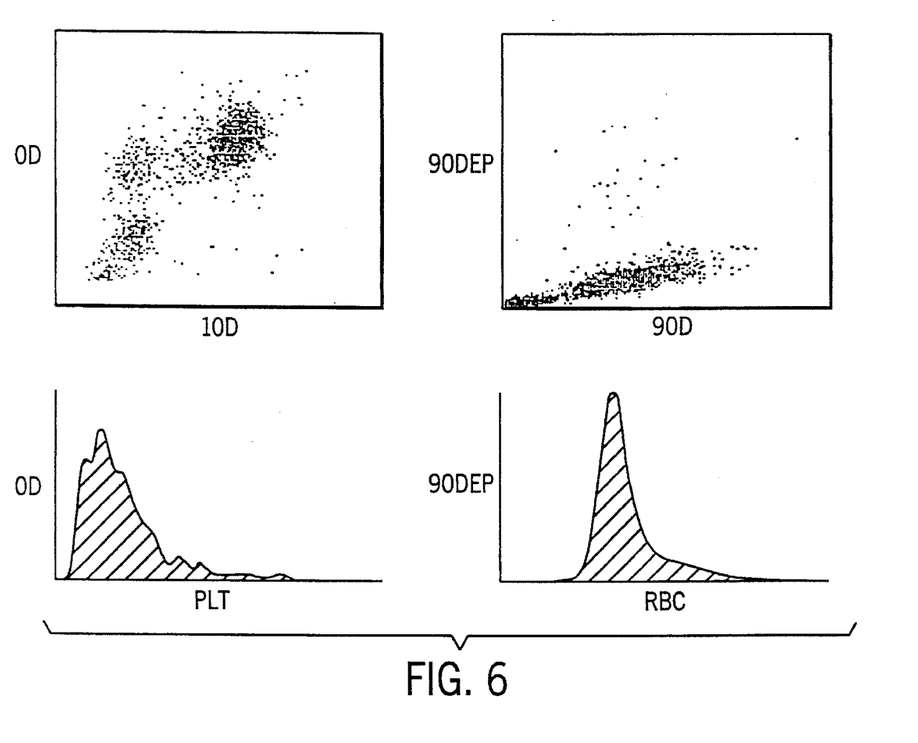

This patient sample was selected because it had elevated levels of monocytes and eosinophils. Previously, these samples were not easily differentiated into five subpopulations because it was difficult to separate and enumerate lymphocytes and monocytes. Using the same axes information as discussed with respect to Example 1, FIG. 5, regions 5 and 6 of FIG. 6 show the enumeration of neutorophils and eisonophils, respectively.

EXAMPLE 3

Figure 7:
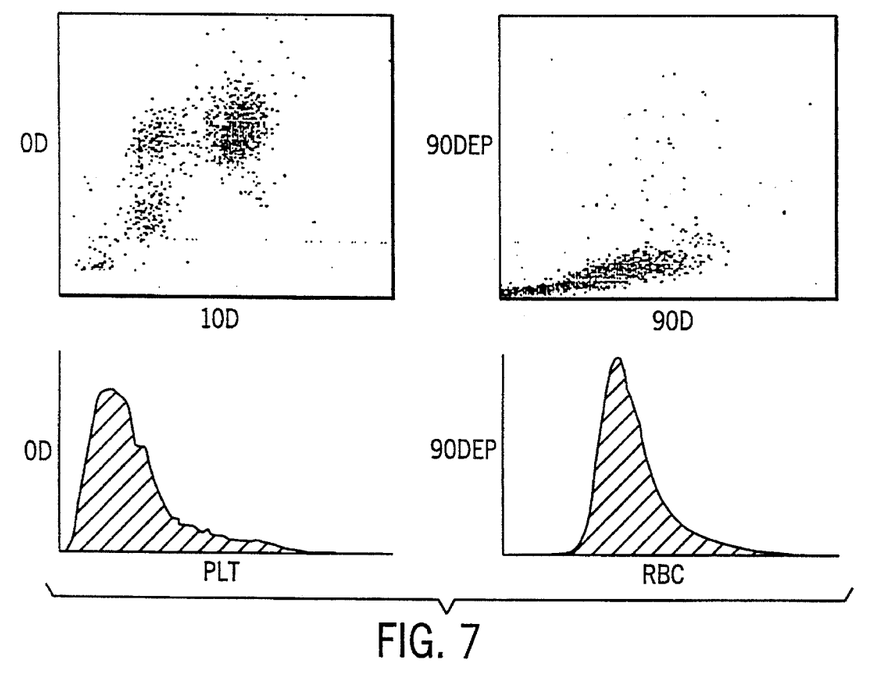
FIG. 7 is a white blood cell scattergram for the whole blood sample described in Example 2.

This patient sample was also selected because it had elevated levels of monocytes and eosinophils. Using the same axes information as discussed with respect to Example 1, FIG. 5, regions 5 and 6 of FIG. 7 show the enumeration of neutorophils and eisonophils, respectively.

EXAMPLE 4

Figure 8:
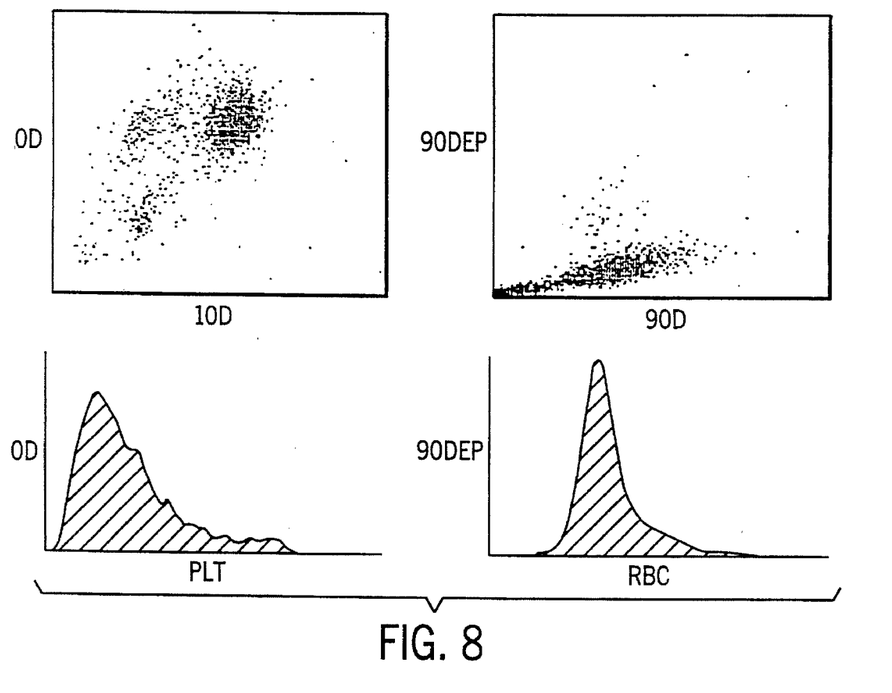
FIG. 8 is a white blood cell scattergram for the whole blood sample described in Example 3.

This patient sample was also selected because it had elevated levels of monocytes and eosinophils. Using the same axes information as discussed with respect to Example 1, FIG. 5, regions 5 and 6 of FIG. 8 show the enumeration of neutorophils and eisonophils, respectively.

While certain representative embodiments and details have been shown for the purpose of illustrating the invention, various changes and modifications can be made therein without departing from the scope of the invention as defined in the appended claims.

What is claimed is:

1. A method for obtaining a five part differential determination of leukocyte cell subpopulations from a whole blood sample, which comprises the steps of:
   a. contacting a whole blood sample containing red blood cells and leukocytes with a diluent;
   b. lysing said red blood cells and sheathing said leukocyte cells by the addition of a flow cytometry lytic agent to said diluted whole blood sample, said flow cytometry lytic agent consisting essentially of:
      (1) an aromatic oxyethanol used in a concentration sufficient to impart leukoprotective properties to the flow cytometry lytic agent;
      (2) an organic buffer with pK at or near 8.5, serving to provide pH buffering capacity and to increase the electrical conductivity of the lytic agent; and,
      (3) a non-ionic detergent component;
   c. intersecting said lysed red blood cells and said sheathed leukocytes with a focussed laser beam;
   d. measuring four light scattering parameters resulting from said intersection at:
      (1) 0 degree light scatter;
      (2) 10 degree light scatter;
      (3) 90 degree light scatter; and
      (4) 90 degree depolarized light scatter; and,
   e. resolving the measured light scattering parameters to obtain a five subpopulation differential enumerating the neutrophils, lymphocytes, monocytes, eosinophils and basophils.

2. The five part differential determination method of claim 1 wherein said aromatic oxyethanol is 2-phenoxyethanol.

3. The five part differential determination method of claim 1 wherein said organic buffer is selected from the group consisting of 2-Amino-2(hydroxymethyl)-1,3-propanediol/ HCl, boric acid, glycylglycine and N,N-bis(2-hydroxyethyl)glycine.

4. The five part differential determination method of claim 1 wherein said non-ionic detergent is selected from the group consisting of octylphenoxypolymethoxyethanol and hydrophilic detergents having polyoxyethylene or saccharide head groups.

5. The five part differential determination method of claim 1 wherein said flow cytometric lytic agent consists essentially of an aqueous solution of 2-phenoxyethanol, 2-Amino-2(hydroxymethyl)-1,3-propanediol/HCl buffer and (octylphenoxypolyethoxyethanol).

6. The five part differential determination method of claim 5 wherein said 2-phenoxyethanol is present at concentration of between 20 mM and 80 mM.

* * * * *